(12) United States Patent
Ewing et al.

(10) Patent No.: US 9,123,520 B2
(45) Date of Patent: Sep. 1, 2015

(54) METHOD FOR SELECTIVE DETECTION OF EXPLOSIVES IN MASS SPECTROMETER OR ION MOBILITY SPECTROMETER AT PARTS-PER-QUADRILLION LEVEL

(75) Inventors: Robert G. Ewing, Kennewick, WA (US); David A. Atkinson, Richland, WA (US); Brian H. Clowers, Richland, WA (US)

(73) Assignee: BATTELLE MEMORIAL INSTITUTE, Richland, WA (US)

( * ) Notice: Subject to any disclaimer, the term of this patent is extended or adjusted under 35 U.S.C. 154(b) by 765 days.

(21) Appl. No.: 13/437,718

(22) Filed: Apr. 2, 2012

(65) Prior Publication Data
US 2013/0260478 A1 Oct. 3, 2013

(51) Int. Cl.
*G01N 33/00* (2006.01)
*H01J 49/14* (2006.01)
*H01J 49/00* (2006.01)
*H01J 49/26* (2006.01)

(52) U.S. Cl.
CPC ............ *H01J 49/14* (2013.01); *G01N 33/0057* (2013.01); *H01J 49/0077* (2013.01); *H01J 49/26* (2013.01)

(58) Field of Classification Search
CPC .. E21B 17/028; E21B 43/166; H01J 49/0027; H01J 49/14; H01J 49/145; H01J 49/165; H01J 49/025; H01J 49/26; G01N 27/622; G01N 27/624; G01N 33/0057
USPC .......................................................... 436/173
See application file for complete search history.

(56) References Cited

U.S. PATENT DOCUMENTS

| | | | |
|---|---|---|---|
| 5,485,016 | A | 1/1996 | Irie et al. |
| 2004/0079879 | A1 | 4/2004 | Ross et al. |
| 2005/0061964 | A1 | 3/2005 | Nagano et al. |
| 2010/0127164 | A1 | 5/2010 | Atkinson et al. |
| 2012/0325024 | A1* | 12/2012 | Vidal-de-Miguel et al. ........................ 73/863.24 |

OTHER PUBLICATIONS

Waltman's PhD Thesis, "Atmospheric Pressure Chemical Ionization Sources Used in the Detection of Explosives by Ion Mobility Spectrometry", May 2010, Pacific Nortwest National Laboratory.*

(Continued)

*Primary Examiner* — Yelena G Gakh
(74) *Attorney, Agent, or Firm* — James D. Matheson

(57) ABSTRACT

A method for selective detection of volatile and non-volatile explosives in a mass spectrometer or ion mobility spectrometer at a parts-per-quadrillion level without preconcentration is disclosed. The method comprises the steps of ionizing a carrier gas with an ionization source to form reactant ions or reactant adduct ions comprising nitrate ions ($NO_3^-$); selectively reacting the reactant ions or reactant adduct ions with at least one volatile or non-volatile explosive analyte at a carrier gas pressure of at least about 100 Ton in a reaction region disposed between the ionization source and an ion detector, the reaction region having a length which provides a residence time (tr) for reactant ions therein of at least about 0.10 seconds, wherein the selective reaction yields product ions comprising reactant ions or reactant adduct ions that are selectively bound to the at least one explosive analyte when present therein; and detecting product ions with the ion detector to determine presence or absence of the at least one explosive analyte.

20 Claims, 7 Drawing Sheets

(56) References Cited

OTHER PUBLICATIONS

Hansel, A., et al., Proton Transfer Reaction Mass Spectrometry: On-Line Trace Gas Analysis at the ppb Level, International Journal of Mass Spectrometry and Ion Processes, 149/150, 1995, 609-619.

Smith, D., et al., Selected Ion Flow Tube Mass Spectrometry (SIFT-MS) for On-Line Trace Gas Analysis, Mass Spectrometry Reviews, 2005, 24, 661-670.

Waltman, M. J., et al., Characterization of a Distributed Plasma Ionization Source (DPIS) for Ion Mobility Spectrometry and Mass Spectrometry, Talanta, 2008, 77, 249-255.

International Search Report/Written Opinion for International Application No. PCT/US2013/020530, International Filing Date Jan. 7, 2013, Date of Mailing Apr. 25, 2013.

Gapeev, A., et al., Liquid chromatography/mass spectrometric analysis of explosives: RDX adduct ions, Rapid Communications in Mass Spectrometry, 17, 2003, 943-948.

Daum, K. A., et al., Resolving interferences in negative mode ion mobility spectrometry using selective reactant ion chemistry, Tananta, 54, 2001, 299-306.

Ewing, R. G., et al., Direct Real-Time Detection of RDX Vapors Under Ambient Conditions, Analytical Chemistry, 85, 2013, 389-397.

* cited by examiner

RDX

Tetryl

PETN

EGDN

NG

METHOD FOR SELECTIVE DETECTION OF EXPLOSIVES IN MASS SPECTROMETER OR ION MOBILITY SPECTROMETER AT PARTS-PER-QUADRILLION LEVEL

STATEMENT REGARDING RIGHTS TO INVENTION MADE UNDER FEDERALLY-SPONSORED RESEARCH AND DEVELOPMENT

This invention was made with Government support under Contract DE-AC05-76RL01830 awarded by the U.S. Department of Energy. The Government has certain rights in the invention.

FIELD OF THE INVENTION

The present invention relates generally to methods and systems for detection of analytes. More particularly, the invention relates to a system and process for selective detection of vapors at atmospheric pressures.

BACKGROUND OF THE INVENTION

Current state of the art trace detection for explosives, chemical threat agents, and other threat agent signatures have remained long-standing goals of modern instrument platforms. However, analytical techniques for direct vapor detection of threat agents remain limited because significant improvements in sensitivity must yet be attained if automated technologies are to be of practical use. For example, equilibrium vapor pressures (saturated) of RDX explosive at 25° C. provide a concentration of ~6 parts-per-trillion (ppt) or 6 in $10^{12}$. Because real-world analyses must achieve detection below saturation levels, sensitivity must be substantially better than this 6 ppt threshold. To complicate matters, improvements in sensitivity without improvements in selectivity are counterproductive, as increasing sensitivity effectively raises the chemical noise, which offsets improvements to upstream components. Thus detection of threat agent vapors requires significant increases in sensitivity along with subsequent increases in selectivity. While some sensitivity and selectivity improvements have been achieved with mass spectrometry (MS)-based analytical approaches including, e.g., Selected Ion Flow Tube (SIFT) Mass Spectrometry (MS) or (SIFT-MS); Proton Transfer Reaction Mass Spectrometry (PTR-MS); and Atmospheric Pressure Chemical Ionization Mass Spectrometry (APCI-MS), none of these approaches provides selective determination of vapors from explosives and other threat agents. Nor do these approaches achieve sensitive and selective trace level detection of threat agents in real-time.

Accordingly new systems and processes are needed that enable real-time trace level detection of explosives and other threat agents at a parts-per-trillion level or better. The present invention addresses these needs.

SUMMARY OF THE INVENTION

A method is described for selective detection of target analytes. The method may include distributing a gas-phase sample containing at least one analyte in a carrier gas at a carrier gas pressure of at least about 100 Torr (0.13 atm) into a reaction region defined between an ionization source and a detector that are separated a selected distance apart in a reaction chamber. The carrier gas is ionized by the ionization source to form reactant ions that include nitrate ($NO_3^-$). Reactant ions have a sufficient residence time in the reaction region to selectively bind with the analyte to form adduct ions. Adduct ions are detected by the detector, which determines whether the analyte is present in the gas-phase sample. Presence of the analyte in the gas-phase sample determines whether the analyte is present, e.g., on a selected contact or measurement surface, or in a surrounding environment.

In another embodiment, the method includes ionizing a carrier gas with an ionization source in a reaction region defined between an ionization source and a detector that are separated a distance apart in a reaction chamber to form reactant ions that include nitrate ($NO_3^-$). By controlling residence time in the reaction region, reactant ions selectively bind with the analyte when introduced in the gas-phase sample forming adduct ions in the reaction region. Adduct ions are detected by the detector to determine the presence or absence of the analyte in the gas-phase sample. Presence of the analyte in the gas-phase sample determines whether the analyte is present, e.g., on a selected contact or measurement surface.

A system is also described for selective detection of gas-phase (target) analytes. The system may include a reaction chamber with an ionization source and a detector located a selected distance apart that defines a reaction region. The reaction chamber may be configured to receive a gas-phase sample in a carrier gas in the reaction region. The ionization source ionizes the carrier gas when introduced into the reaction region at a pressure above 100 Torr (0.13 atm) that forms reactant ions including nitrate ($NO_3^-$). The reaction region provides a sufficient residence time for the reactant ions to preferentially or selectively bind to the at least one analyte when introduced into the reaction region in the carrier gas that yields chemical adducts between the reactant ions and the target analyte. The detector is configured to detect the chemical adduct ions that identifies the presence of the at least one analyte in the gas-phase sample introduced into the reaction chamber.

In some embodiments, the carrier gas pressure is at least about 100 Torr (0.13 atm).

In some embodiments, residence time of the reactant ions in the reaction region is at least about 0.10 seconds. In some embodiments, residence time of the reactant ions is between about 0.10 seconds and about 30 seconds. In some embodiments, residence time is selected between about 0.10 seconds and about 3 seconds. In some embodiments, residence time is selected above about 3 seconds. In some embodiments, residence time is selected between about 3 seconds and about 30 seconds.

In some embodiments, forming adduct ions includes providing a number of collisions between the reactant ions and the carrier gas containing the target analyte of between about 5E+08 collisions and about 1E+13 collisions prior to the detection of the adduct ions. In some embodiments, forming adduct ions includes flowing the carrier gas to control residence time of the reactant ions in the reaction region.

In some embodiments, forming adduct ions includes applying an electric field along the length between the ionization source and the detector to control residence time of the reactant ions in the reaction region. In some embodiments, the electric field is a dynamic electric field. In some embodiments, the electric field is a static electric field. In some embodiments, forming adduct ions includes simultaneously applying an electric field and a flow of carrier gas to control residence time of the reactant ions in the reaction region.

In some embodiments, the reactant ions have a selectivity for binding to the at least one analyte that is greater than the selectivity for binding to another constituent when present in the reaction region.

In some embodiments, the analyte may include an explosive and/or an explosive compound. Explosives and explosive compounds include, but are not limited to, e.g.: nitroamines; nitrate esters; cyclotrimethylenetrinitramine (RDX); pentaerythritol tetranitrate (PETN); 2,4,6-Trinitrophenylmethylnitramine (TETRYL); SEMTEX, C4, nitroglycerin (NG); ethylene glycol dinitrate (EGDN); cyclotetramethylene-tetranitramine (HMX); other chemical explosives vapors; including combinations of these various explosives and explosives compounds. In some embodiments, the analyte may be an explosive taggant such as 2,3-dimethyl-2,3-dinitrobutane (DMDNB).

In some embodiments, the analyte may be introduced into the reaction chamber from a swipe sample.

In some embodiments, the analyte may be introduced into the reaction region from such items as luggage or baggage. In some embodiments, the analyte may be introduced into the reaction region from cargo items. In some embodiments, the analyte may be introduced into the reaction region from a person or a surrounding gas. In some embodiments, the analyte may be introduced into the reaction region from a gas sample collected in a selected environment. In some embodiments, the analyte may be introduced into the reaction chamber in a gas different than, or separate from, the carrier gas. In some embodiments, the analyte may be introduced into the reaction chamber by differential pressure.

In some embodiments, the analyte concentration may be at or below about 100 parts-per-trillion (ppt). In some embodiments, the analyte concentration may be in the range from about 100 parts-per-trillion to about 1 part-per-trillion. In some embodiments, the analyte concentration may be in the range from about 1 part-per-trillion to about 0.01 parts-per-trillion. In some embodiments, the analyte concentration may be in the range from about 0.01 parts-per-trillion to about 0.001 parts-per-trillion.

In some embodiments, detecting adduct ions may include monitoring a detection signal for the adduct ions with the detector. In some embodiments, the method may include optimizing the detection signal for the adduct ions by adjusting the number of collisions between the reactant ions and the carrier gas containing the at least one analyte in the reaction region until the detection signal for the adduct ions formed between the reactant ions and the at least one target analyte is above background. In some embodiments, optimizing the detection signal may include adjusting an operating parameter including, but not limited to, e.g., electric field; carrier gas composition; carrier gas flow rate; residence time of the reactant ions; number of collisions between the reactant ions and the carrier gas containing the analyte; and combinations of these operating parameters.

In some embodiments, the carrier gas may be air. In various embodiments, the carrier gas may include a gas selected from nitrogen, argon, helium, oxygen, carbon dioxide, or combinations of these various gases.

In some embodiments, increasing the length of the reaction region provides a time that allows the reactant ion to form adduct ions with target analytes of interest without increasing background noise because the selected reactant ion does not react with most species.

In various embodiments, the ionization source for ionizing the carrier gas may be selected from: static electric discharge sources; varying electric discharge sources; plasma torch sources; photoemission ionization sources; electrospray ionization sources; or photoionization sources. In some embodiments, the ionization source may be a radioactive decay ionization source. In some embodiments, the radioactive decay ionization source may be a $^{63}Ni$ ionization source. In some embodiments, the ionization source may be a non-radioactive ionization source. In various embodiments, the ionization source for ionizing the carrier gas may be selected from: pulsed ionization sources; time-varying discharge sources (e.g., dielectric barrier discharge sources); corona ionization sources; LED ionization sources; and combinations of these various ionization sources.

In some embodiments, the reactant ions in the reaction region may be nitrate ($NO_3^-$) ions (m/z=62). In some embodiments, the reactant ions in the reaction region may be nitrate-containing adduct ions including, e.g., [$NO_3^-$. $HNO_3$] with mass number (m/z=125); [$NO_3^-$.($H_2O$)$_x$ where x=1 to 4, with mass numbers (m/z=80), (m/z=98), (m/z=116), and (m/z=134)], and like adducts. In other embodiments, reactant ions may be chloride ($Cl^-$) ions, bromide ($Br^-$) ions, iodide ($I^-$) ions, nitrite ($NO_2^-$) ions, or adducts of these ions.

In some embodiments, the flow of carrier gas in the reaction region located between the vapor sample inlet and/or a carrier gas inlet and the sample detector may provide mixing of a sample containing an explosive or explosive compound vapor with the carrier gas delivered at atmospheric pressure.

In some embodiments, a sample detector may be coupled at, or in proximity to, an exit to the reaction chamber in order to detect the analyte vapor. The reaction region can include a length that in operation provides a sufficient number of collisions between the reactant ions and the carrier gas containing explosive or explosive compound vapors to form a sufficient concentration of negative chemical adduct ions for detection that identifies the presence of the explosive or the explosive compounds in the gas sample.

In some embodiments, the system may include a sample inlet and a carrier gas inlet for mixing and introducing an analyte vapor in a carrier gas into the reaction region.

In some embodiments, the ionization source may be coupled adjacent the carrier gas inlet to ionize the carrier gas delivered through the carrier gas inlet into the reaction region to form the reactant ion.

In some embodiments, analytes may be delivered to the reaction region upstream from the ionization source. In some embodiments, analytes may be delivered to the reaction region downstream from the ionization source.

In some embodiments, the detector may be a mass spectrometer. In some embodiments, the detector may be an Ion Mobility Spectrometer (IMS) or a Differential Mobility Spectrometer (DMS).

The purpose of the foregoing abstract is to enable the United States Patent and Trademark Office and the public generally, especially the scientists, engineers, and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

DETAILED DESCRIPTION

A system and process are described for selective detection of analyte vapors including those from explosives at various concentrations. "Low concentration" as used herein means an analyte concentration at or below about 100 parts-per-trillion (ppt) when introduced in a carrier gas at selected carrier gas pressures above 100 Torr (0.13 atm). While preferred embodiments of the present invention will be described, from the description, it will be apparent that various modifications, alterations, and substitutions may be made without departing from the scope of the invention as set forth in the claims listed hereafter. Further, while the present invention will be described in reference to detection of chemical explosives, the invention is intended to cover various and multiple threat agents, as well as chemicals used to identify the presence of threat agents including explosive taggants such as 2,3-dimethyl-2,3-dinitrobutane (DMDNB). Accordingly, the description of the preferred embodiments should be seen as illustrative only and not limiting.

Figure 1:
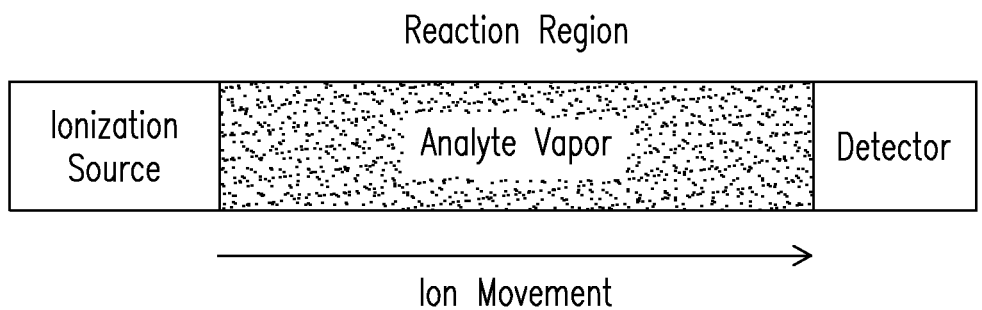
FIG. 1 shows a simplified system for detection of analytes according to one embodiment of the invention.

FIG. 1 shows a simplified system for selective detection of target analytes. The system includes a reaction chamber configured with an ionization source and a detector. A reaction region may be defined between the ionization source and the detector. In an exemplary and non-limiting configuration, the reaction chamber may be of a tube design with a length dimension greater than the cross-section (e.g., diameter) dimension. The tube may be constructed of a selected metal (e.g., copper). In one exemplary construction, the outer diameter (O.D.) may be 2.54 cm (1 inch), the length may be 71.1 cm (28 inches), and the inner diameter (I.D.) may be 2.36 cm (0.93 inches). The reaction chamber may be coupled to a mass-selective detector for detection of the analyte vapor, as detailed hereafter.

In some embodiments, the reaction region may be defined between the ionization source and the detector. A gas-phase sample may be introduced into the chamber in a carrier gas that distributes within the reaction region equalizing the concentration of the vapor within the reaction region. Carrier gases include, but are not limited to, e.g., air, nitrogen ($N_2$), argon (Ar), helium (He), oxygen ($O_2$), carbon dioxide ($CO_2$), other inert gases, and combinations of these various gases. In a preferred embodiment, the carrier gas includes ambient air. In some embodiments, the ionization source may be located adjacent to, and in front of, the reaction region, but position is not intended to be limited. Pressures of the carrier gas in the reaction region are preferably over 100 Torr. The ionization source ionizes the carrier gas in the reaction region. Ionization of the carrier gas by the ionization source produces reactant ions that are selective (i.e., preferentially or selectively bind to) for target analytes of interest when present in the gas-phase sample introduced to the reaction region. The reaction region may be of a length that provides reactant ions a residence time sufficient to form chemical adduct ions with the analyte molecules present in the carrier gas. Reaction parameters that maximize the number of collisions between the reactant ions and the carrier gas containing the target analytes of interest include, but are not limited to, e.g., flow rate of the carrier gas, pressure (P) of the carrier gas, residence time (t) of the reactant ions, electric field (E), and combinations of these various parameters. For example, by controlling the residence time of reactant ions in the reaction region, the ion signal of chemical adduct ions can be optimized. Chemical adduct ions are subsequently delivered to, or detected in, a detector, where the detection signal for chemical adduct ions of interest may be monitored and determined. The detector determines the presence or absence of the chemical adduct ion. Optimizing the detection signal for the chemical adduct ions when present includes adjusting the number of collisions between the reactant ions with the carrier gas containing the target analytes until the detection signal for the chemical adduct ions is above the signal background. Presence of the (ion) detection signal for the chemical adduct ions identifies the presence of the target analyte (e.g., explosives) in the gas-phase sample. In some embodiments, for example, using this approach, explosives vapors (analyte) can be detected at a concentration better than 100 parts-per-quadrillion (100 parts in $10^{15}$ parts) in less than 30 seconds. In some embodiments, explosives vapors (analyte) may be detected at a concentration better than 100 parts-per-quadrillion (100 parts in $10^{15}$ parts) in less than 10 seconds, as discussed further herein.

Ion Kinetics and Collision Probability

"Sensitivity" measures the detector response to specific analyte concentrations. Relationship between the target analyte concentration (e.g., explosives and threat agent vapors), residence time of reactant ions in the reaction region, and the detection (detector) sensitivity for chemical adduct ions may be given by Equation [1], as follows:

$$[A^-]=[R^-]_0[A]^{kt}, \qquad [1]$$

Here, [A] is the concentration of analyte ions (measured signal); $[R]_0$ is the initial reactant ion concentration (measured signal); [A] is the concentration of the analyte in the carrier gas (units of molecule $cm^{-3}$); (k) is the reaction rate constant (approximately $2\times10^{-9}$ $cm^3$ $molecule^{-1}$ $sec^{-1}$); and (t) is the residence time for reactant ions in the reaction region.

When analyte concentration is plotted as a function of signal intensity, sensitivity may be given by the slope of the line. Since (k) is a constant, increasing the residence time lowers the detection limit. With a fixed ratio of $[A^-]/[R^-]_0$, lower concentrations of [A] can be detected by increasing (t). Increasing residence time (t) can thus provide the necessary sensitivity. However, increasing sensitivity for all components in the reaction region also increases chemical noise, which increases the background signal. In such instances, signal-to-noise ratio remains the same and detection limits are not increased. Thus, an increased selectivity may be needed as well. "Selectivity" assesses the preferential ionization and formation of chemical adducts for one target analyte compared with another. Selectivity results in a relative increase in the number of chemical adduct ions that are formed with a specific and desired target analyte compared with the comparatively large number of benign carrier or other background molecules.

Ionization Sources

Figure 2:
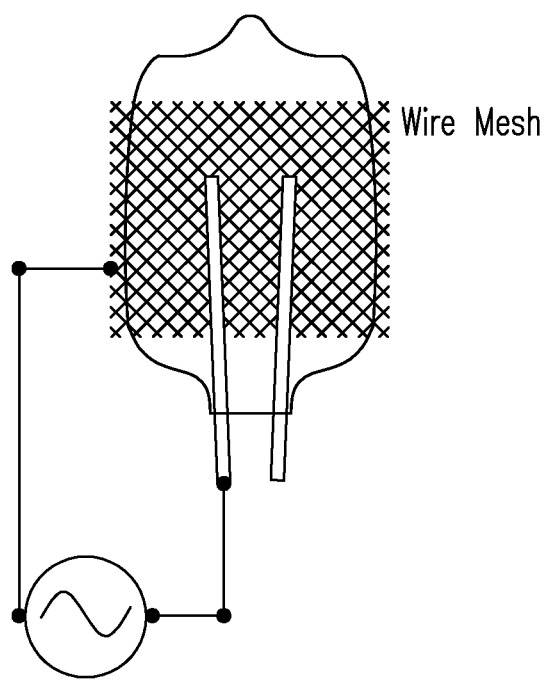
FIG. 2 shows a preferred ionization source for ionization of analytes, according to one embodiment of the invention.

FIG. 2 shows an exemplary ionization source of a Dielectric Barrier Discharge Ionization (DBDI) type used in concert with the invention. The ionization source includes a glass bulb filled with neon gas, or another excitation gas. Gas selection is not limited. The bulb includes at least two electrodes that provide excitation of the neon (or other enclosed) gas in the bulb. Supporting electronics provide power to the bulb to generate the ion (i.e., conductive) plasma. In some embodiments, the bulb may be illuminated with a DC current. In some embodiments, the bulb may be illuminated with an AC current.

In some embodiments, the glass bulb includes an external surface containing a dielectric material in which the bulb serves as a primary conductor dielectric medium. In the present embodiment, the bulb includes a metal mesh (e.g., stainless steel mesh) placed in close proximity to, or in contact with a dielectric material (not shown) on the exterior surface of the bulb. The wire mesh provides a large surface area from which plasma discharges can originate.

In some embodiments, one electrode serves as a primary electrode and the wire mesh serves as a secondary electrode. In the instant embodiment, a conductive plasma may be generated with a single bulb electrode connected as shown. Other bulb ion sources typically require connection of two bulb electrodes to generate a plasma.

In some embodiments, when a high (~kHz) frequency alternating current (AC) is placed across the single electrode that is connected to the bulb, and the conducting mesh (e.g., stainless steel) electrode located external to the bulb, a plasma discharge may be generated at the edges of the external conducting electrode. Discharge of the plasma occurs when the voltage potential between the conducting electrode and the plasma within the bulb reaches the break-down voltage of the gas at a given temperature, pressure, and humidity.

In various embodiments, the selected ionization source can be operated in a pulsed, continuous, or variable manner depending on the applied waveform or the combination of electric waveforms applied. The circuit that drives the ionization source remains functional because the dielectric material prevents a true electric short from occurring while still enabling the discharge.

In typical operation, discharge by the ionization source in the reaction region initially produces free electrons. However, when a sufficient carrier gas density is present, electrons are transferred to the gas medium which forms reactant ions, described further herein. Reactant ions then react with analyte vapors upon collision in the reaction region, forming chemical adduct (target) ions of interest.

Other ionization sources have also been demonstrated in conjunction with the present invention. In one embodiment, a corona discharge source may be used, in which a voltage potential may be placed between an electrode point (e.g., a tip of a needle) and a metal surface of the reaction chamber (e.g., a copper tube). The ionization source produces reactant ions (e.g., $NO_3^-$ and/or other $NO_3^-$ containing species), which collide with analyte vapors in the reaction region, as described herein, forming chemical adduct ions with analyte vapors of interest.

While exemplary ionization sources have been described, the invention is not intended to be limited thereto. Ionization sources suitable for use with the present invention include, but are not limited to, e.g., $^{63}Ni$ sources, corona sources; corona discharge sources; Distributed Plasma Ionization Sources (DPIS); open DPIS sources; enclosed DPIS sources; Electrospray Ionization (ESI) sources; Atmospheric Pressure Ionization (API) sources; Atmospheric Pressure (AP) Chemical Ionization (APCI) sources; AP Glow Discharge Ionization (GD) (APGD) sources; AP Photo Ionization sources; Dielectric Ionization sources (DIS); Dielectric Barrier Discharge Ionization (DBDI) sources; Dielectric Plasma Ionization (DPI) sources; Dielectric Isolated Plasma Ionization sources; Photoemission Ionization Sources; components of these various sources; and combinations of these sources and components.

Other ionization sources and conditions can be employed to generate stabilized gas phase ions that may or may not include nitrogen for the detection of other compound classes including, but not limited to, e.g., narcotics, toxic industrial chemicals and materials, and chemical threat agents. No limitations are intended.

Figure 3:
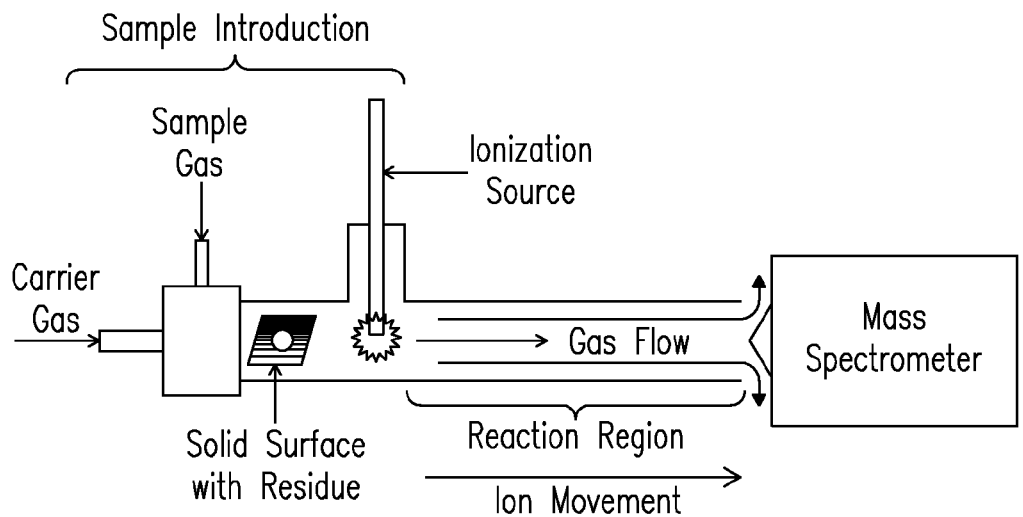
FIG. 3 shows a system for detection of analytes, according to another embodiment of the invention.

FIG. 3 shows another embodiment of the system of the present invention for detection of target analytes. In the figure, analyte vapors may be introduced to the reaction region in various ways. In some embodiments, a sample gas including one or more analyte vapors of interest may be introduced to the reaction region (e.g., through a sample gas inlet). In some embodiments, a solid surface containing a surface residue(s) may be placed in front of the reaction region. In some embodiments, a solid surface containing a solid sample may be placed in front of the reaction region. Samples containing, e.g., explosives residues can also be introduced into the reaction region in front of the ionization source, e.g., on various surfaces including, but not limited to, e.g., sample slides, sample swipes, and/or other solid surfaces. In some embodiments, a carrier gas can be flowed over a surface containing a surface residue. In some embodiments, a carrier gas may be used to introduce analyte vapors into the reaction region. Flow rates are not intended to be limited. In other embodiments, solid samples (e.g., a powder on a solid surface) serve to introduce the analyte vapor into the reaction region in front of the ionization source. In some embodiments, the ionization source may be located in the reaction region downstream from where samples are introduced, but position is not intended to be limited. The ionization source vaporizes some fraction of the carrier gas or ambient gas in the reaction region producing reactant ions. Samples introduced as vapors can be carried by way of carrier gas, e.g., from a carrier gas source, into the reaction region. For example, in the solid residue configuration, carrier gas flows over the top of the residue on the solid surface, carrying a portion of any vapor emanating from the residue located on the solid surface into the reaction region as a vapor. Explosives vapors introduced into the reaction region from either the vapor gas sample or the residue sample collide with reactant ions present in the gas phase of the reaction region and react with explosives vapors when present in the sample forming a negative chemical adduct that defines the ionized explosive detected subsequently in the mass spectrometer. Excess carrier gas exits the reaction region immediately prior to the inlet of the mass spectrometer, but exit location is not limited thereto as will be understood by those of ordinary skill in the mass-spectrometry instrument arts.

Figure 4:
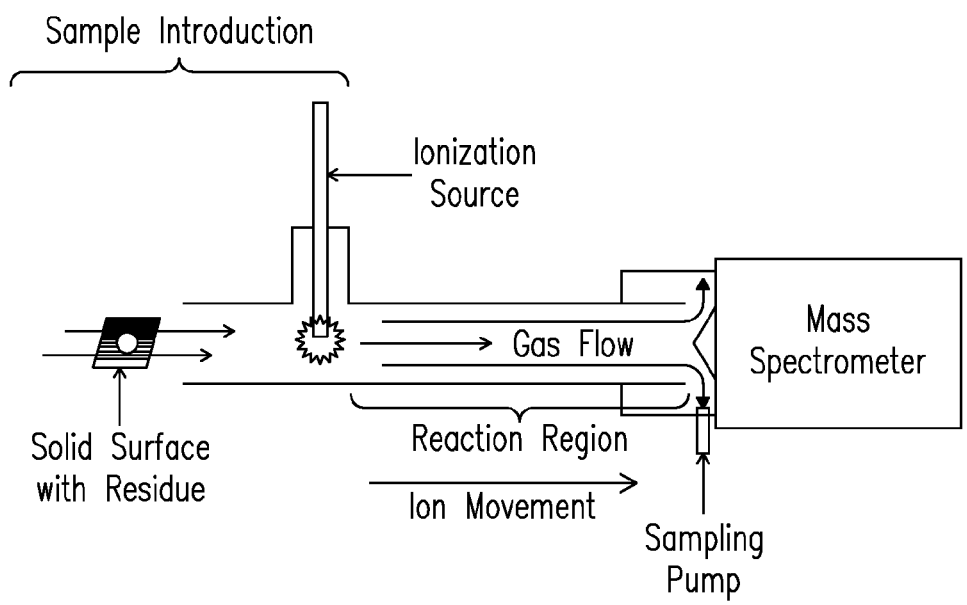
FIG. 4 shows a system for detection of analytes, according to yet another embodiment of the invention.

FIG. 4 shows a system according to another embodiment of the present invention for detection of target analytes. In the figure, a sampling pump may be positioned along the reaction region that pulls air through the reaction region. Thus, a source of carrier gas is not required. This configuration provides direct sampling of vapors collected from any surface (baggage, clothing, etc.) placed in front of the inlet to the reaction region that introduces the vapor samples into the reaction region. In some embodiments, enclosures (e.g., an air chamber) can be installed in front of the inlet to the reaction region permitting residues from cargo, luggage, and people to be collected and tested in the system. Collected explosives vapors are introduced as vapors in ambient air directly into the system in front of the ionization source without need of a supplied carrier gas. In the present embodiment, air drawn into the system can be subsequently removed from the reaction region by pumping air from the system, e.g., with a pump placed immediately prior to the inlet of the mass spectrometer, but location for pumping gas is not intended to be limited thereto as will be understood by those of ordinary skill in the mass-spectrometry instrument arts.

Figure 5:
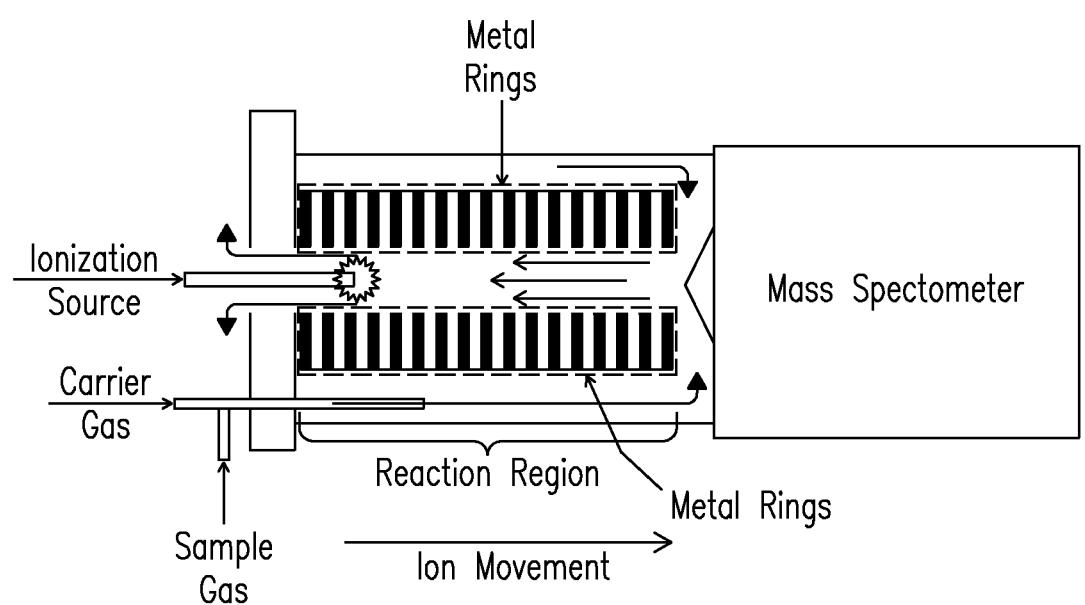
FIG. 5 shows a system for detection of analytes, according to still yet another embodiment of the invention.

FIG. 5 shows a system according to still yet another embodiment of the present invention for detection of target analytes. In the figure, the reaction region may include a series of "stacked" metal rings with central ring openings (~2" I.D.). Each ring is separated by a dielectric material. Dielectric materials include, but are not limited to, e.g., polytetrafluoroethylene (PTFE), ceramics, quartz, glass, boron nitride, or another insulating material. The metal rings are electrically connected to a series of resistors that establishes a voltage gradient between the ionization source and the mass spectrometer (detector). Voltages applied to the rings establish an electrical field that moves ions in the reaction region from the ionization source to the detector. Electrical field strength may be varied. In some embodiments, field strength may be varied in the reaction region from about 2000 V (100 V/cm) to about 100 V (5 V/cm), but field strength is not intended to be limited thereto. Voltage gradient can be adjusted to increase the ion residence time or decrease the ion residence time in the reaction region. Voltages are selected such that residence times for reactant ions in the reaction region are sufficient to form chemical adduct ions between reactant ions and selected explosives vapors, as described herein. Chemical adduct ions are subsequently detected to determine presence of explosives in the gas samples (e.g., for items being inspected).

Reactant Ions

Preferred reactant ions are those that selectively or preferentially bind with target analytes of interest including, e.g., chemical explosive and threat agent vapors. Reactant ions that form selective stabilizing gas-phase complexes and/or selective chemical adduct ions can also be used. Preferred reactant ions are also non-reactive with chemical species other than the target analyte of interest when introduced in a sample gas into the reaction region. TABLE 1 lists electron affinities for typical reactant ions.

TABLE 1

Electron affinities of typical reactant ions at API conditions.*

| Species | Electron Affinity (eV) |
|---|---|
| $NO_3^-$ | 3.7-3.9 |
| $Cl^-$ | 3.6 |
| $NO_2^-$ | 1.8-3.9 |
| $O_3^-$ | 1.8-2.5 |
| $CO_3^-$ | 1.8-3.5 |
| $O_2^-$ | 0.40-1.3 |

*Ranges obtained from NIST at: (http://webbook.nist.gov/chemistry/form-ser.html).

Reactant ions include nitrate ($NO_3^-$) (m/z=62) and nitrate-containing adduct ions. Nitrate-containing adduct ions include, but are not limited to, e.g., [$NO_3^-$.$HNO_3$] (m/z=125); and [$NO_3^-$.($H_2O$)$_x$] where x=1 to 4 (m/z=80, 98, 116, and 134, respectively).

In some embodiments, nitrate ($NO_3^-$) ions (m/z=62) may be preferred reactant ions in the reaction region given their selective binding to target analytes of interest. Nitrate ($NO_3^-$) has a high electron affinity that does not give up charge easily to most species in the gas phase. In particular, the present invention can capitalize upon the stability of nitrate ions to form chemical adducts (selective complexes) with target analytes including, e.g., gas-phase explosives and other threat agents described hereafter. $NO_3^-$ may be created from any suitable discharge ionization source at selected pressures above 100 Torr. Electron affinity of the nitrate reactant ion means that the nitrate ion is not expected to give up its negative charge or otherwise participate in charge-exchange reactions. Thus, selectivity is achieved since the only ionization mechanism available is the formation of chemical adducts between the nitrate reactant ion and the target analyte of interest. Further, selectivity is achieved since few analytes have a propensity to share this charge and to form stable adduct ions. Thus, a reduction in chemical background is achieved while yielding chemical adduct ions with the analytes of interest.

In some embodiments, reactant ions in the reaction region may be nitrate-containing adduct ions including, e.g., [$NO_3^-$.$HNO_3$] with mass number (m/z=125); [$NO_3^-$.($H_2O$)$_x$ where x=1 to 4, with mass numbers (m/z=80), (m/z=98), (m/z=116), and (m/z=134)], and like adducts. In other embodiments, reactant ions may be chloride ($Cl^-$) ions, bromide ($Br^-$) ions, iodide ($I^-$) ions, nitrite ($NO_2$) ions, or adducts of these ions.

Explosive and Explosive Compounds

Target analytes detected in concert with the invention include chemical explosives, composite explosives (e.g., SEMTEX and C4), chemicals used to identify presence of explosives [e.g., explosive taggants such as 2,3-dimethyl-2,3-dinitrobutane (DMDNB)] and other threat agents. "Explosives" and "explosive compounds" encompass any chemical substance or compound that when heated or struck undergoes a rapid chemical change, producing a gas that leads to a sudden reactive outburst (explosion). In some embodiments, the explosives or explosive compounds include a nitroamine chemical backbone. In some embodiments, the explosives or explosive compounds include a nitrate ester chemical backbone.

Figure 6:
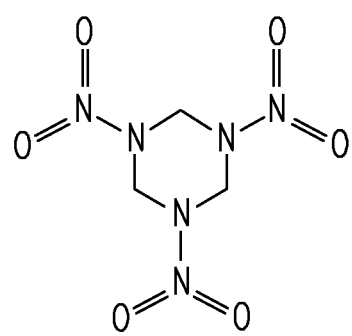
FIG. 6 shows chemical structures of exemplary explosives and explosive compounds detected in conjunction with the invention.
Figure 6:
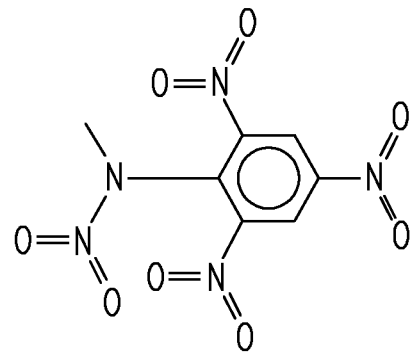
Figure 6:
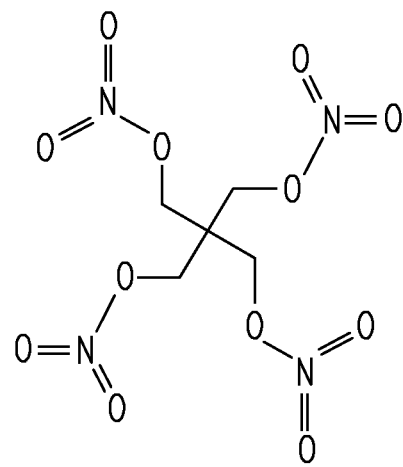
Figure 6:
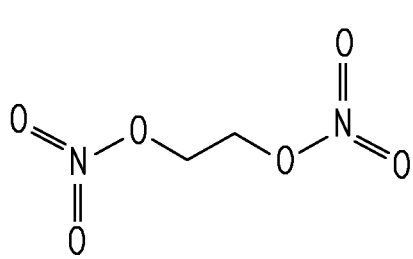
Figure 6:
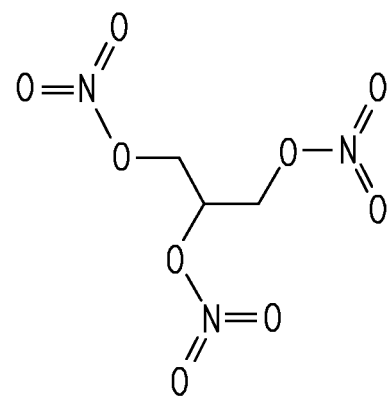

FIG. 6 shows chemical structures of exemplary and selected explosives that incorporate these backbones. Explosives include, but are not limited to, e.g., pentaerythritol tetranitrate (PETN); cyclotrimethylenetrinitramine (RDX); SEMTEX (including, e.g., SEMTEX-1A, SEMTEX-H, SEMTEX-2P, and analogues) is a general purpose plastic explosive containing RDX (e.g., up to about 41% by weight) and PETN (e.g., from about 40% to about 80% by weight), as well as plasticizers (e.g., n-octyl phthalate or tributyl citrate), binders (e.g., styrene-butadiene), stabilizers (e.g., N-phenyl-2-napthylamine), and dyes (e.g., diazo dye); C4 is a plastic explosive containing RDX, a plasticizer (e.g., n-octyl phthalate or tributyl citrate), and a binder (e.g., styrene-butadiene); 2,4,6-Trinitrophenylmethylnitramine (TETRYL) also known as N-methyl-N,2,4,6-tetranitroaniline; nitroglycerin (NG); ethylene glycol dinitrate (EGDN); cyclotetramethylene-tetranitramine (HMX); and other chemical explosives vapors at selected pressure conditions can be achieved.

Residence Times

Residence (reaction) time of reactant ions in the reaction region may be controlled to provide a sufficient (or selected)

number of collisions that achieves successful formation of chemical adduct ions between reactant ions and target analytes present in the carrier gas at a selected carrier gas pressure. Residence time of reactant ions can be a function of parameters including, but not limited to, e.g., length of the reaction region, number of collisions in the reaction region prior to detection, carrier gas flow, carrier gas pressure, electric field voltage, electric field strength, including combinations of these various process parameters, described further herein.

In some embodiments, residence times required to form chemical adducts between reactant ions and analyte vapors (e.g., chemical explosives) are between about 0.10 seconds and about 30 seconds. In some embodiments, residence times required to form chemical adducts between reactant ions and analyte (e.g., explosives) vapors are between about 0.10 seconds and about 3 seconds. In some embodiments, residence times for forming chemical adducts between reactant ions and analyte (e.g., explosives) vapors are above about 3 seconds. In some embodiments, residence times for forming chemical adducts are selected between about 3 seconds and 30 seconds. No limitations are intended.

Collisions

Collisions in the reaction region between reactant ions and carrier gas molecules that include target analyte molecules may be governed both by the pressure of the carrier gas and the time it takes reactant ions to move through the carrier gas in the reaction region. Rate constants for formation of chemical adduct ions vary depending on properties of the reactant ions and the surrounding carrier gas molecules. Rate constants for adduct ion formation reactions described herein may be on the order of about $2 \times 10^{-9}$ cm$^3$ molecule$^{-1}$ second$^{-1}$ (estimated). For example, at atmospheric pressure (760 Torr) and a temperature of 25° C., number density of carrier gas molecules in the reaction region is about $2.5 \times 10^{19}$ molecules per cm$^3$. Thus, at these conditions, a reactant ion can experience about $5 \times 10^{10}$ collisions in one second (as defined by the product of the gas number density, the collision rate constant, and the time) with other molecules in the reaction region. This gives a reactant ion about 1 in 20 chances (~5%) of colliding with an analyte molecule at an analyte concentration of 1 in $10^{12}$ molecules (or 1 part-per-trillion). Since many reactant ions originate from the ion source, statistically, analyte ions in this example, should represent roughly 5% of the total ion signal at an analyte concentration of 1 part-per-trillion (ppt) assuming that adduct ion formation (i.e., ionization) occurs at every collision between the reactant ion and the analyte molecule. Detection sensitivity for the chemical adduct ion (and thus the analyte) may thus be a function of the number of collisions in the reaction region between the reactant ions and the carrier gas molecules containing the analytes. The more collisions a reactant ion experiences increases the probability that the reactant ion will collide with an analyte of interest in the surrounding carrier gas. Lower pressures and/or shorter ion residence times in the reaction region will result in higher (poorer) detection limits, whereas higher pressures and/or longer ion residence times in the reaction region will result in lower (better) detection limits. For example, by increasing the reaction time or pressure by a factor of 10 in the example above (i.e. 10 seconds or 10 atm), a detection of 100 parts-per-quadrillion (100 in $10^{15}$) detection may be achievable with the same analyte signal ratio of 5%. Number of collisions may be between about $6 \times 10^8$ collisions (at a pressure of 100 Torr and a residence time of 100 milliseconds) to about $7 \times 10^{12}$ collisions (at a pressure of 5 atm and a residence time of 30 seconds). Those of ordinary skill in the art will appreciate that more collisions in the reaction region can enable a better sensitivity, but a longer residence time can come at a cost of a lower total ion current. Selectivity of the reactant ions for the analyte of interest also affects formation of chemical adduct ions in the reaction region.

Carrier Gas Pressures

Pressures of the carrier gas in the reaction region can range from about 0.13 atm (about 100 Torr) to about 5 atmospheres. In some embodiments, pressure of the carrier gas in the reaction region may be up to 760 Torr. In some embodiments, pressure of the carrier gas in the reaction region may be from about 5 Torr to about 760 Torr. In some embodiments, pressure of the carrier gas in the reaction region may be below 760 Torr. In some embodiments, pressure of the carrier gas may be above 760 Torr (1 atm). In some embodiments, pressure of the carrier gas may be between about 1 atm and 4 atm. No limitations are intended.

Carrier Gas Flow Rates

Carrier gas flow rates can be varied to control residence time of reactant ions in the reaction region. In some embodiments, carrier gas flow may be used alone to control residence time. In some embodiments, carrier gas flow may be used in combination with applied electric fields to control residence time of reactant ions in the reaction region, as detailed further herein. In some embodiments, carrier gas flow rates are between about 1 liter per minute and about 5 liters per minute, but flow rates are not intended to be limited. For example, in some embodiments, carrier gas flow rates are between about 0.5 cm/sec to about 50 cm/sec.

Electric Field Voltages

Electric Fields can also be applied along the length of the reaction region between the ion source and the detector to control residence times of the reactant ions in the reaction region. In some embodiments, the electric field may be a dynamic electric field. In some embodiments, the electric field may be a static electric field. In some embodiments, electric field voltages may be selected between about 0.01 Volts/cm to about 500 Volts/cm. In some embodiments, electric field voltages may be selected between about 0.1 Volts/cm to about 200 Volts/cm. In some embodiments, electric field voltages may be selected between about 1 Volts/cm to about 100 Volts/cm. No limitations are intended.

In some embodiments, both an electric field and a carrier gas flow may be applied to control residence time of reactant ions in the reaction region (see discussion, FIG. 5). In some embodiments, an electric field and a carrier gas flow may be applied simultaneously.

Figure 7:
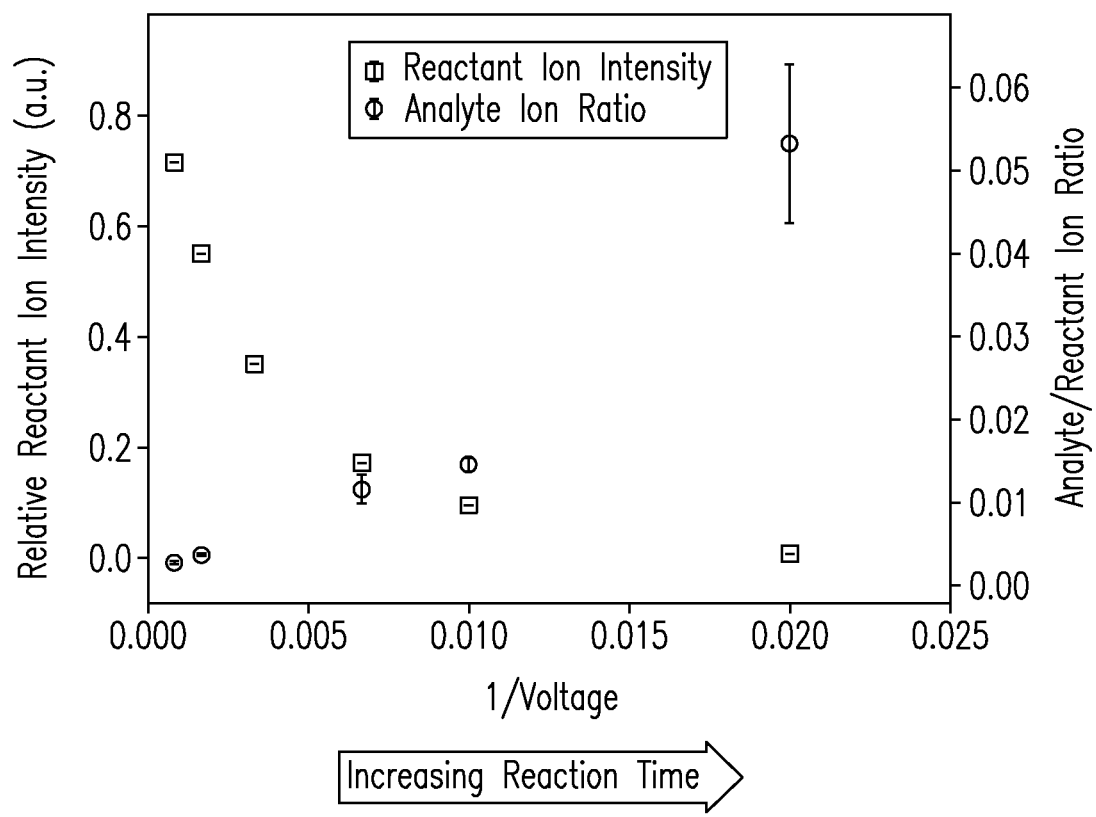
FIG. 7 plots reactant ion intensity as a function of voltage against the analyte-to-reactant ion ratio used to determine optimum residence time needed to form chemical adduct ions between the reactant ion and a target analyte.

FIG. 7 plots the reactant ion intensity as a function of the reciprocal applied voltage (1/V) and the ratio of the target analyte signal intensity (e.g., an explosive compound) to the reactant ion as a function of the reciprocal applied voltage (1/V). The plot shows the relationship between total reactant ion intensity (signal), analyte-to-reactant ion ratio (analyte signal), and reactant ion residence times in the reaction region (X-axis). Residence times required for reactant ions to form chemical adducts of interest in the reaction region may be selected where the analyte-to-reactant ion ratio is above zero, and where sufficient reactant ion intensity exists. All residence times that meet these requirements may be selected. Thus, no limitations are intended.

Detectors

When detected, chemical adduct ions formed in the reaction region identify the presence of explosive vapors in the initial gas sample. Any detector capable of detecting and/or determining chemical adducts ions described herein may be used without limitation. In some embodiments, the detector may be a mass-selective detector, e.g., a mass spectrometer. In other embodiments, the detector may be an Ion Mobility Spectrometer (IMS) or a Differential Mobility Spectrometer (DMS). No limitations are intended.

Signal Intensity

Figure 8:
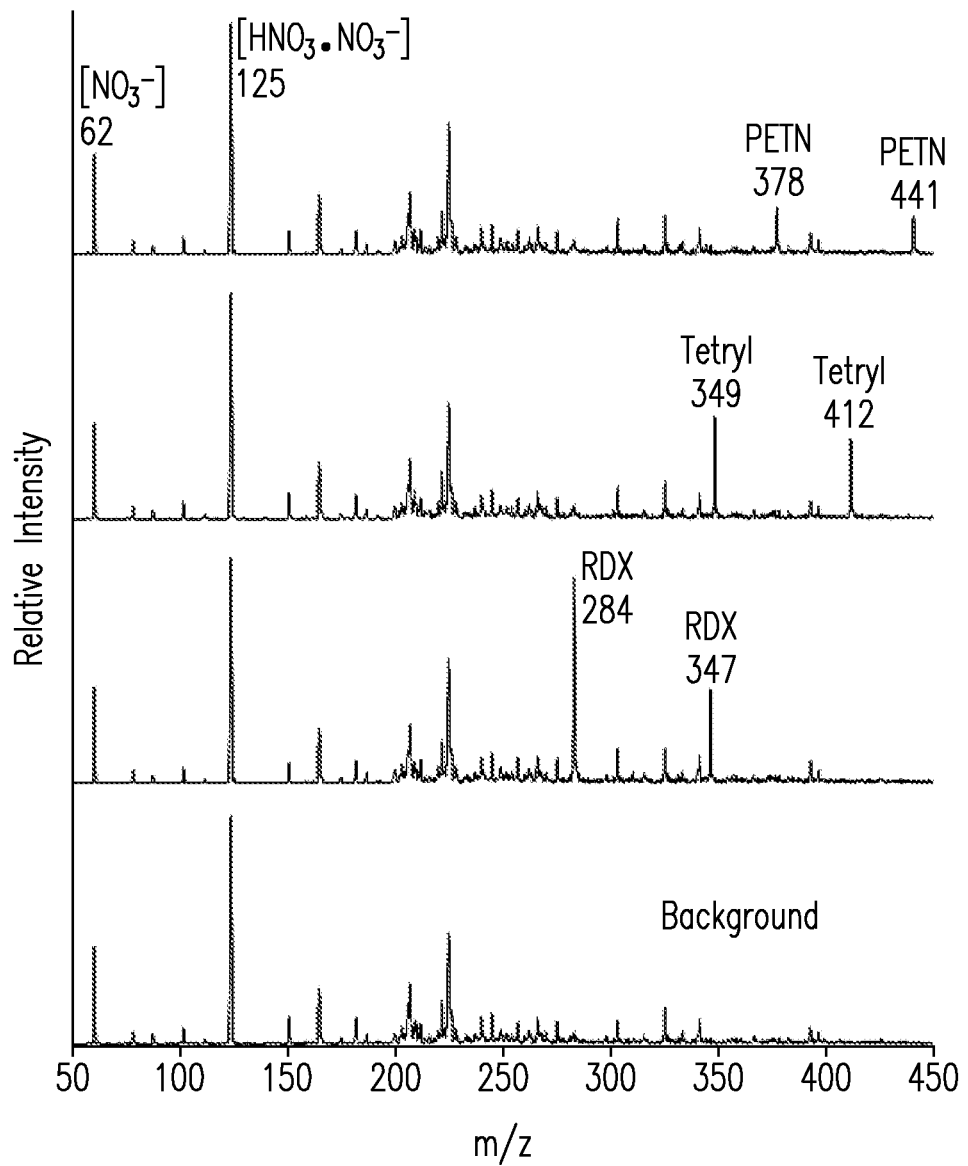
FIG. 8 shows peak intensities of selected explosive vapors detected in concert with the invention.

[FIX] FIG. 8 compares relative peak intensities of exemplary chemical adduct ions formed between nitrate ($NO_3^-$) reactant ions and selected explosives vapors (target analytes) against the background spectrum. The intensity of the background spectrum, RDX spectrum, TETRYL spectrum, and PETN spectrum above m/z=200 are magnified by a factor of 20 to better show the signal intensities relative to the reactant ion peak intensities (at m/z=62 and m/z=125). Results show that background signals are relatively and comparatively low. In the RDX spectrum, two peaks at m/z=284 and m/z=347, representing nitrate adducts of RDX, are significantly above background, which provides vapor detection for RDX. In the TETRYL spectrum, peaks detected at m/z=349 and m/z=412, representing nitrate adducts of TETRYL, provides vapor detection for TETRYL in the sample. And, in the PETN spectrum, peaks detected at m/z=378 and m/z=441, representing nitrate adducts of PETN, provides vapor detection for PETN.

Figure 9:
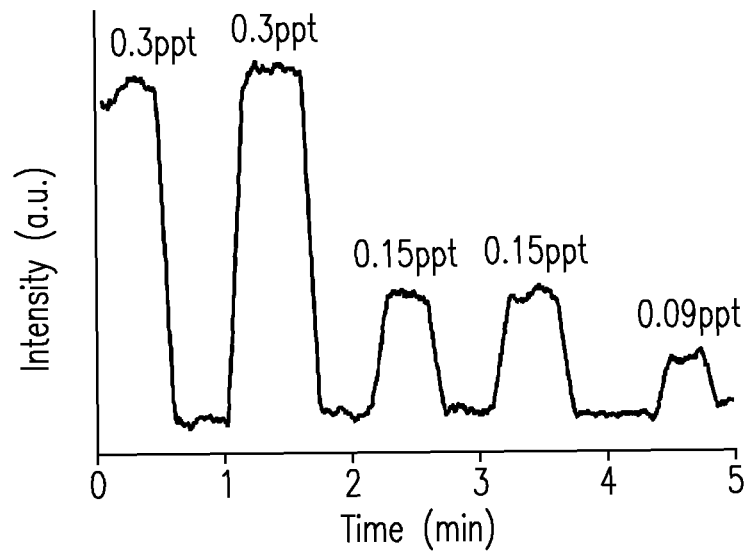
FIG. 9 shows Selective Ion Monitoring (SIM) ion intensity peaks for an RDX-nitrate adduct at different concentrations as a function of time.

FIG. 9 shows Selective Ion Monitoring (SIM) of the RDX-nitrate adduct ion intensity as a function of time. RDX-nitrate adduct ion (m/z=284) was monitored by monitoring the signal strength at m/z=284. Different concentrations of RDX were presented to the system, with concentrations toggled "on" and "off". When no RDX analyte was introduced into the reaction region (i.e., "off" position), signal of the RDX-nitrate adduct ion dropped to a low, consistent level. Results show an ability to detect levels of RDX vapor at concentrations below 100 parts-per-quadrillion. Vapor detection of the explosive vapor was performed at ambient conditions with results obtained in less than 10 seconds.

Figure 10:
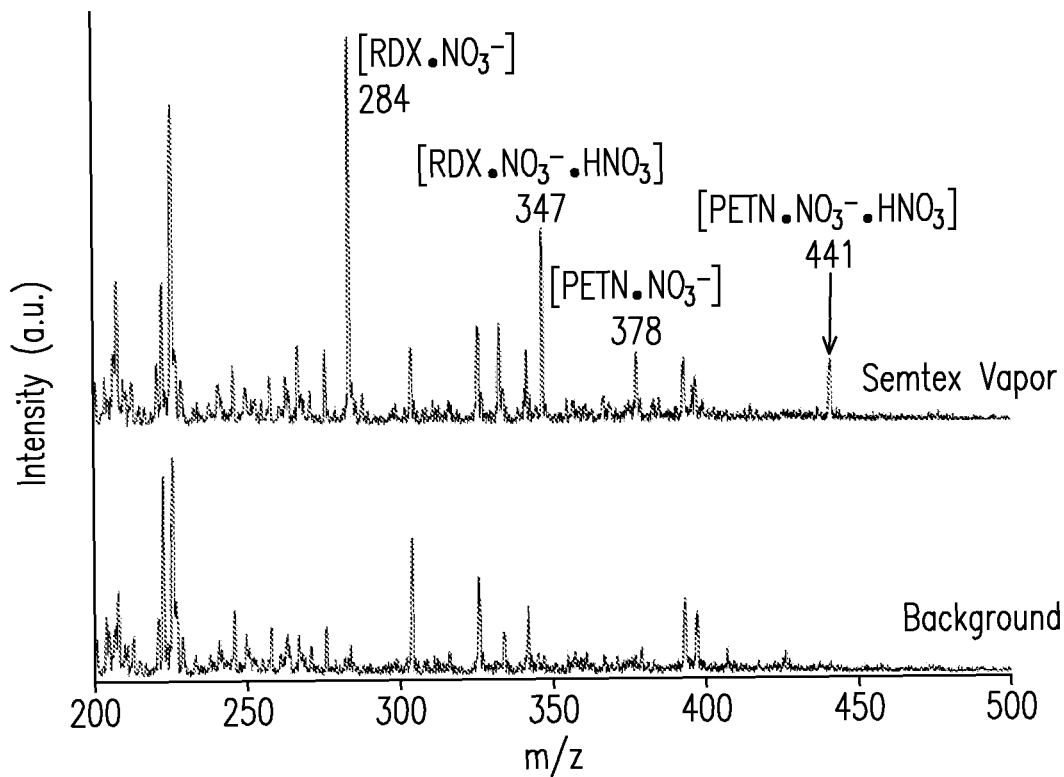
FIG. 10 shows peak intensities for vapors of composite explosives detected in concert with the invention.

FIG. 10 shows peak intensities for different explosives vapors detected in a vapor sample of a composite (more than one) explosive (e.g., SEMTEX). Despite presence of binders and plasticizers in the composite explosive, vapors of both RDX and PETN are detectable in the SEMTEX vapor sample. Multiple adduct signatures can be used to minimize the false positive rate (FPR). For example, as discussed previously for FIG. 8, two (2) discrete reactant ions, e.g., nitrate ($NO_3^-$) at m/z=62 and a nitrate adduct (e.g., $NO_3^-$. $HNO_3$) at m/z=125, form adducts with explosive compounds, including those in composite explosives and mixtures of explosives. Here, RDX (m/z=222) combines with both reactant ions to form adducts. Adduct peaks of RDX are observed at m/z=284 [m/z=62 ($NO_3^-$)+m/z=222 (RDX)] and m/z=347 [m/z=125 ($NO_3^-$.$HNO_3$)+m/z=222 (RDX)]. These 2 identifying peaks confirm the presence of RDX in the vapor sample. Adduct peaks of PETN are also observed at m/z=378 [m/z=62 ($NO_3^-$)+m/z=316 (PETN)] and m/z=441 [m/z=125 ($NO_3^-$.$HNO_3$)+m/z=316 (PETN)].

The following Examples provide a further understanding of the invention.

EXAMPLE 1

Detection of RDX Vapor Introduced in a Carrier Gas

In one experiment, detection of RDX vapor was demonstrated. The system of FIG. 3 was used absent the solid surface with residue in a reaction chamber in a reaction region positioned between a custom discharge ionization source (FIG. 2) and a triple quadrupole mass spectrometer detector. RDX vapor was introduced into the reaction region through the sample gas inlet. Saturated RDX vapor was generated by applying 50 pg of RDX (e.g., 50 µL of a solution of RDX in methanol at a concentration of 1 mg/mL) to 50 mg of quartz wool in a 3-inch (7.62 cm) long ¼-inch (0.64 cm) O.D. stainless steel tube and allowing the methanol to evaporate leaving RDX residue. Compressed air was passed through the tube containing RDX coated quartz wool at a few hundred mL/min to establish a source of air saturated with RDX vapor equal to approximately 6 parts-per-trillion. A second flow of air was added to the carrier inlet to dilute and mix with the RDX vapor and introduce the diluted vapor past the ionization source into the reaction region all contained within a 1-inch (2.54 cm) O.D. copper tube with a reaction region of length 28 inches (71.1 cm). RDX was detected as a nitrate adduct peak (m/z=284) by the mass spectrometer. Intensity of the RDX adduct peak (m/z=284) was monitored using Selected Ion Monitoring (SIM) as a function of time. RDX sample flows of 200, 100 and 60 mL per minute were delivered through the sample gas inlet and mixing with the carrier gas at a rate of 3800 mL/min to produce concentrations of 0.3 $ppt_v$, 0.15 ppt, and 0.09 $ppt_v$ respectively. FIG. 9 shows the instrument response at these various concentrations.

EXAMPLE 2

Detection of RDX Vapor

The system of FIG. 3 was used in concert with a solid surface containing sample residues. About 30 pg RDX, TETRYL, and PETN were separately placed on a 1-inch (2.54 cm) square glass slide in a sample solution in methanol and then evaporating the solvent, leaving the sample residues on the glass slide. A reaction chamber constructed of a tube with a 1-inch (2.54 cm) outer diameter (O.D.) dimension contained the ionization source, which was followed by a reaction region of a 28-inch (71.12 cm) length. The tube was coupled to a triple quadrupole mass spectrometer, which was used as a detector. The glass slide containing the sample residues was placed in the reaction chamber. Room air (carrier gas) was pulled through the reaction chamber at a rate of approximately 2 L/min to move sample vapors from the slide surface through the ionization source into the reaction region. FIG. 8 shows signal peaks for RDX, TETRYL, and PETN detected by the mass spectrometer.

EXAMPLE 3

Detection of RDX Vapor in a Carrier Gas

The system of FIG. 5 was used. A stack of metal rings approximately 20 cm in length were electrically coupled to control ion residence times in the reaction region. In one test, 50 pg RDX (e.g., 50 µL of a solution of RDX in methanol at a concentration of 1 mg/mL) was applied to 50 mg of quartz wool in a 3-inch (7.62 cm) long, ¼-inch (0.635 cm) O.D. stainless steel tube and the methanol was allowed to evaporate. Compressed air (carrier gas) was passed through the tube containing the RDX coated quartz wool at a rate of 3 L/min to saturate the air with RDX vapor at a concentration of ~6 parts-per-trillion. Carrier gas containing RDX vapor was introduced into the reaction region in a direction countercurrent to the ion flow. Electrical field strength was varied by varying voltages applied to the metal rings from 2000 V to 100 V (or 100 V/cm to 5 V/cm), establishing an electric field which caused the nitrate reactant ions to move from the source to the triple quadrupole mass spectrometer (detector). Lower voltages resulted in longer ion residence times through the reaction region, yielding more RDX-nitrate adduct ions (and signal) relative to the reactant ion signal. Higher voltages provided shorter ion residence times through the reaction region. Residence times for reaction between the explosive vapor and reactant ions were varied from tens of milliseconds to a few seconds. Reactant ions and RDX-nitrate adduct ions were detected by the mass spectrometer. FIG. 7 presents results.

EXAMPLE 4

Detection of Explosives Mixtures and Composites

The system of FIG. 3 was used. Samples containing about 2 mg of SEMTEX (or C4) solid on a glass slide were placed in the reaction chamber constructed of a 1 inch (2.54 cm) (O.D.) tube. The chamber contained an ionization source followed by a reaction region of a 28-inch (71.12 cm) length. The reaction chamber was coupled to a triple quadrupole mass spectrometer. A carrier gas of air was supplied to the reaction chamber at a rate of ~4 L/min. Carrier gas swept the vapors of the explosive compounds from the glass slide into the reaction region. PETN and RDX from the SEMTEX sample were detected by the mass spectrometer. FIG. 8 presents spectra. Similar results were obtained for C4.

EXAMPLE 5

Other Analyte Signatures

Detection of analyte vapors from a mixture containing various compounds was demonstrated. The system of FIG. 4 was used. The reaction chamber was constructed of a tube with a 1-inch (2.54 cm) outer diameter (O.D.) dimension which contained the ionization source, and a reaction region of 28-inch (71.12 cm) length. A chemical solution was prepared that included ~0.1 mg of each analyte in acetone. Analytes in the solution included: nicotine, dimethyl methylphosphonate, diisopropyl methylphosphonate, thiodiglycol, methylphosphonic acid, and isopropyl methyl phosphonic acid. The solution was applied to a 1 cm×1 cm×5 cm concrete surface and allowed to dry at room temperature prior to analysis. The concrete surface was held ~1 cm from the entrance of the reaction chamber. Room air (carrier gas) was pulled through the reaction chamber at a rate of approximately 2 L/min to move sample vapors from the concrete surface through the ionization source into the reaction region. After exit from the reaction region, ions were sampled using a triple quadrupole mass spectrometer, which served as a detector. Adducts of nitrate ions included both molecular adducts with the nitrate and/or nitrate adducts of molecular degradation products.

While exemplary embodiments of the present invention have been shown and described, it will be apparent to those skilled in the art that many changes and modifications may be made without departing from the invention in its true scope and broader aspects. The appended claims are therefore intended to cover all such changes and modifications as fall within the spirit and scope of the invention.

What is claimed is:

1. A method for selective detection of volatile and non-volatile explosives in a mass spectrometer or ion mobility spectrometer at a parts-per-quadrillion level without preconcentration, comprising the steps of:

ionizing a carrier gas with an ionization source to form reactant ions or reactant adduct ions comprising nitrate ions ($NO_3^-$);

selectively reacting the reactant ions or reactant adduct ions with at least one volatile or non-volatile explosive analyte at a carrier gas pressure of at least about 100 Torr in a reaction region disposed between the ionization source and an ion detector, the reaction region having a length which provides a residence time ($t_r$) for reactant ions therein of at least about 0.10 seconds and is defined by the equation:

$$t_r = \frac{(L)}{(V_g) + (V_E)} = \frac{(L)}{(V_g) + (K \times E)}$$

where:

(L) is length of the reaction region (cm);

($V_g$) is reactant ion linear velocity due to flow of carrier gas ($cm \cdot s^{-1}$);

($V_E$) is reactant ion linear velocity due to applied electric field ($cm \cdot s^{-1}$);

(K) is mobility of reactant ions at carrier gas pressure and temperature ($cm^2 \cdot V^{-1} \cdot s^{-1}$);

(E) is electric field strength ($V \cdot cm^{-1}$);

wherein the selective reaction yields product ions comprising reactant ions or reactant adduct ions that are selectively bound to the at least one explosive analyte when present therein; and detecting product ions with the ion detector to determine presence or absence of the at least one explosive analyte.

2. The method of claim 1, wherein the reactant ions have a selectivity for binding to said at least one explosive analyte greater than the selectivity for binding to any other constituent present in said reaction region.

3. The method of claim 1, wherein the residence time of the reactant ions and/or the reactant adduct ions in the reaction region is between about 0.10 seconds and about 30 seconds.

4. The method of claim 1, wherein forming the product ions includes a number of collisions between each of the reactant ions and the carrier gas containing the at least one analyte from about 5E+08 to about 1E+13 in the reaction region before detection.

5. The method of claim 1, wherein forming the product ions includes flowing the carrier gas at a flow rate selected from about 0.2 L/min to about 200 L/min to control residence time of the reactant ions in the reaction region.

6. The method of claim 1, wherein forming the product ions includes applying a dynamic electric field or a static electric field along the length between the ion source and the ion detector with an electric field strength selected from about 1 V/cm to about 100 V/cm to control residence time of the reactant ions in the reaction region.

7. The method of claim 1, wherein the at least one explosive analyte includes an explosive, an explosive compound, an explosive taggant, an explosive composite, or combinations thereof.

8. The method of claim 1, wherein the at least one explosive analyte is introduced into the reaction region from a swipe sample.

9. The method of claim 1, wherein the at least one explosive analyte is introduced into the reaction region in a gas separate from the carrier gas.

10. The method of claim 1, wherein the at least one explosive analyte is introduced into the reaction region by differential pressure.

11. The method of claim 1, wherein detecting the product ions includes monitoring a detection signal for the product ions with the ion detector.

12. The method of claim 1, wherein detecting the product ions includes optimizing the detection signal for the product ions by adjusting the number of collisions between said reactant ions and/or said reactant adduct ions and said carrier gas containing said at least one explosive analyte in said reaction region until the detection signal is above background.

13. The method of claim 12, wherein optimizing the detection signal includes adjusting an operating parameter selected from the group consisting of: electric field; carrier gas composition; carrier gas flow rate; residence time of reactant ions; number of collisions between the reactant ions and the carrier gas containing the at least one explosive analyte; and combinations thereof.

14. The method of claim 1, wherein the carrier gas is selected from the group consisting of: nitrogen, argon, helium, oxygen, carbon dioxide, and combinations thereof.

15. The method of claim 1, wherein detecting the product ions includes detecting the at least one explosive analyte at a concentration below about 100 parts-per-trillion.

16. The method of claim 1, wherein detecting the product ions includes detecting the at least one explosive analyte at a concentration of at least about 0.001 parts-per-trillion.

17. The method of claim 1, wherein the gas flow rate defines a linear velocity for the reactant ions or reactant adduct ions in the reaction region selected from about 0.6 cm/sec to about 710 cm/sec.

18. The method of claim 1, wherein detecting the product ions includes detecting with an ion detector selected from a mass-selective detector, a mass spectrometer, an ion mobility spectrometer, a differential mobility spectrometer, and combinations thereof.

19. The method of claim 1, wherein the linear velocity of the reactant ions due to gas flow is: a positive value when gas flow in the reaction region is in a direction toward the ion detector; is a negative value when gas flow in the reaction region is in a direction away from the ion detector; and is a zero value when no gas flows in the reaction region.

20. The method of claim 1, wherein the linear velocity of the reactant ions due to electric field is: a positive value when voltage at the detector end of the reaction region is more positive than voltage at the ionization end of the reaction region; is a negative value when voltage at the detector end of the reaction region is less positive than voltage at the ionization end of the reaction region; and is a zero value when no electric field is applied in the reaction region.

* * * * *